(12) United States Patent
Curtis

(10) Patent No.: US 10,232,184 B2
(45) Date of Patent: Mar. 19, 2019

(54) EXTRACORPOREAL UNIT FOR INSPECTING THE INSULATION OF AN ELECTRICAL WIRE OF AN IMPLANTED MEDICAL DEVICE

(75) Inventor: Guy P. Curtis, San Diego, CA (US)

(73) Assignee: THE GUY P. CURTIS AND FRANCES L. CURTIS TRUST, San Diego, CA (US)

( * ) Notice: Subject to any disclaimer, the term of this patent is extended or adjusted under 35 U.S.C. 154(b) by 81 days.

(21) Appl. No.: 13/607,309

(22) Filed: Sep. 7, 2012

(65) Prior Publication Data

US 2013/0310887 A1 Nov. 21, 2013

Related U.S. Application Data

(60) Provisional application No. 61/649,057, filed on May 18, 2012.

(51) Int. Cl.
| | |
|---|---|
| A61N 1/00 | (2006.01) |
| A61N 1/37 | (2006.01) |
| A61N 1/39 | (2006.01) |
| A61B 5/0424 | (2006.01) |
| A61N 1/08 | (2006.01) |
| G01R 31/12 | (2006.01) |

(52) U.S. Cl.
CPC ............ *A61N 1/371* (2013.01); *A61B 5/0424* (2013.01); *A61N 1/37* (2013.01); *A61N 1/3943* (2013.01); *A61B 2560/0276* (2013.01); *A61N 2001/083* (2013.01); *G01R 31/1227* (2013.01)

(58) Field of Classification Search
USPC ........................................................ 607/119
See application file for complete search history.

(56) References Cited

U.S. PATENT DOCUMENTS

| | | | | |
|---|---|---|---|---|
| 3,349,324 | A | * 10/1967 | Wakefield | ...................... 324/514 |
| 5,383,913 | A | * 1/1995 | Schiff | .............................. 607/38 |
| 5,859,922 | A | 1/1999 | Hoffmann | |

(Continued)

OTHER PUBLICATIONS

PCT International Search Report, Application No. PCT/US2013/040190, dated May 8, 2013.

(Continued)

*Primary Examiner* — Eric D. Bertram
*Assistant Examiner* — Elizabeth K So
(74) *Attorney, Agent, or Firm* — Nydegger & Associates

(57) ABSTRACT

A system is provided for testing the electrical integrity of an implanted pacemaker or defibrillator lead. The system includes a container holding an electrically conductive solution, such as a saline solution. A voltage source and two electrodes are provided to pass an electrical current through the solution. To use the system, the proximal end of the electrical lead is disconnected from the implanted electronic device, passed through the saline solution and then electrically connected to a device/monitor. During testing, the device/monitor sends a test pulse through the lead and monitors electrical activity in the lead. To test sequential locations along the length of the proximal segment, the segment is drawn through the saline solution and between the electrodes while test pulses are sent and monitored. The monitor detects abnormal electrical activity in the lead indicative of a break in lead insulation.

18 Claims, 3 Drawing Sheets

(56) References Cited

U.S. PATENT DOCUMENTS

| | | | |
|---|---|---|---|
| 7,454,249 B1* | 11/2008 | Bornzin | A61N 1/37 607/27 |
| 2004/0162593 A1* | 8/2004 | Jorgenson et al. | 607/27 |
| 2010/0057174 A1* | 3/2010 | Harrison et al. | 607/115 |
| 2010/0174348 A1* | 7/2010 | Bulkes et al. | 607/116 |

OTHER PUBLICATIONS

Wiggins, Biodegradation of Polyether Polyurethane Inner Insulation in Bipolar Pacemaker Leads, article, Jan. 18, 2001, pp. 302-307, John Wiley & Sons, Inc., USA.

* cited by examiner

US 10,232,184 B2

EXTRACORPOREAL UNIT FOR INSPECTING THE INSULATION OF AN ELECTRICAL WIRE OF AN IMPLANTED MEDICAL DEVICE

This application claims the benefit of U.S. Provisional Patent Application Ser. No. 61/649,057, filed May 18, 2012.

FIELD OF THE INVENTION

The present invention pertains generally to medical devices. More particularly, the present invention pertains to test equipment for inspecting insulation in bipolar pacemaker leads. The present invention is particularly, but not exclusively, useful as a device for inspecting a proximal segment of a pacemaker lead while a distal segment of the lead remains operationally positioned in a patient's body.

BACKGROUND OF THE INVENTION

The implantation of a medical device, such as a pacemaker and/or defibrillator, for the purposes of stimulating and/or controlling the heart muscle activity of a patient, involves positioning one or more electrical leads inside the body of the patient. Specifically, these electrical leads extend through the body between a subcutaneously positioned electronic device and the heart.

Although each electrical lead is essentially unitary along its length, different segments of a lead are subjected to different functional environments. For one, the distal segment of the electrical lead, which is placed in direct contact with the heart muscle, must be held relatively stationary. On the other hand, the proximal segment of the electrical lead, which is electrically connected with the electronic device (e.g. a pacemaker or defibrillator pulse generator), must be flexible and responsive to the physical activity of the patient. To effectively establish these different environments (i.e. stability and flexibility), the proximal and distal segments of the electrical lead are separated by a so-called "tie down" which effectively stabilizes only the distal segment of the electrical lead.

For a proper operation of the medical device, it is essential that the electrical integrity of each implanted lead(s) be maintained, and uncompromised, throughout its entire length. As a practical matter, due to the activity that is typically experienced in the proximal segment of the electrical lead, this segment is more susceptible to damage. This proximal segment, however, is more easily accessible and, indeed, can be accessed without adversely disturbing the stability of the distal segment. Nevertheless, both segments (proximal and distal) should be periodically checked for their electrical integrity. When and how this is to be done will be best left to the judgment of the attending physician.

With the above in mind, it is an object of the present invention to provide a system and method for testing the electrical integrity of a proximal segment of an electrical lead that is used with an implanted medical device. It is another object of the present invention to provide a device for inspecting a proximal segment of a pacemaker or defibrillator lead while a distal segment of the lead remains operationally positioned in a patient's body. Yet another object of the present invention is to provide an extracorporeal unit for inspecting the insulation of an electrical wire of an implanted medical device and corresponding methods of use which are easy to use, relatively simple to implement, and comparatively cost effective.

SUMMARY OF THE INVENTION

In accordance with the present invention, a system is provided for testing the electrical integrity of an elongated lead when the lead is used with an implanted electronic device to stimulate/control heart muscle activity of a patient. For example, the electronic device may be a pacemaker pulse generator/sensor, defibrillator pulse generator/sensor or a combination pacemaker/defibrillator. As envisioned for the present invention, the elongated lead that is to be tested by the system of the present invention defines an axis, is formed with a central lumen, and has insulated electrode wires which extend between a proximal end and a distal end of the lead. In the context of the present invention, the electrical lead is used to establish an electrical connection between the electronic device and the heart muscle of the patient.

Structurally, the system of the present invention includes a monitor that is electrically connected to the proximal end of the lead during testing. This is an electrical connection, and its purpose is for monitoring electrical activity in the lead. The monitor can be of any type well known in the pertinent art that is capable of performing the required functions described herein.

As described further below, for pacemaker dependent patients, a monitor/pulse generator is electrically connected to the proximal end of the lead during testing. The purpose of the monitor/pulse generator is essentially two-fold. For one, the monitor/pulse generator is used to send a test pulse and/or pacing pulse through the lead. For the other purpose, the monitor/pulse generator is used for monitoring electrical activity in the lead. This dual function component (i.e. monitor/pulse generator) can be of any type well known in the pertinent art that is capable of performing the required functions.

In a first embodiment of the present invention, the system also includes a container that has a wall surrounding a chamber. Specifically, the container is provided to hold an electrically conductive fluid, such as a saline solution. PAlso included in combination with the container is a voltage source. Structurally, the voltage source has both a cathode and an anode that are respectively connected to the wall of the container. With this connection, the voltage source is used to thereby establish an electrical current through the solution in the chamber. Typically, the voltage source is a pulsed voltage source.

For an operation of this embodiment, the proximal end of the electrical lead is first disconnected from the implanted electronic device (e.g. pacemaker pulse generator). Then, the proximal end of the electrical lead is inserted through an access port that is formed in the wall of the container and is passed through the saline solution. Next, the proximal end of the electrical lead is electrically connected to the monitor (or in the case of a pacemaker dependent patient, the monitor/ pulse generator). Once connected to the monitor, and with the voltage source activated to produce a current in the solution, the proximal segment of the electrical lead is drawn, portion by portion, through the solution. As this is done, an interrupt signal will be received by the monitor indicating that the electrical lead is defective whenever there is a break in the lead insulation.

For pacemaker dependent patients, test/pacing signals can be sent through the lead during the procedure to the patient by the monitor/pulse generator. As this is done, an interrupt signal will be received by the monitor whenever the current in the saline solution interferes with the test/pacing signal. Specifically, the monitor will receive an interrupt signal indicating that the electrical lead is defective whenever there is a break in the lead insulation.

After a test has been performed, the monitor/pulse generator can be disconnected from the proximal end of the electrical lead. If the electrical lead is determined to be operationally sound, the electrical lead can again be connected with the medical device. Otherwise, the electrical lead will need to be replaced.

In another embodiment of the present invention, a portion of the lead is tested while the portion remains implanted in a subcutaneous pocket of a patient. For this embodiment, the electrically conductive solution is disposed within the subcutaneous pocket of the patient. Also for this embodiment, the anode and cathode of the voltage source are spaced-apart and attached to a non-conductive tip of a retractor. With the proximal end of the electrical lead electrically connected to the monitor, the retractor tip is immersed in the electrically conductive solution to generate a current, e.g. pulsed current, in the solution. To improve electrical coupling, the tip of the retractor can be L-shaped to align the anode and cathode in a direction substantially parallel to a plane containing a portion of the lead undergoing testing. As the current is generated in the solution, an interrupt signal will be received by the monitor indicating that the electrical lead is defective if there is a break in the lead insulation. For a pacemaker dependent patient, the monitor is replaced by a monitor/pulse generator as described above. For this case, an interrupt signal will be received by the monitor whenever the current in the saline solution interferes with the test/pacing signal. Specifically, the monitor will receive an interrupt signal indicating that the electrical lead is defective whenever there is a break in the lead insulation.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
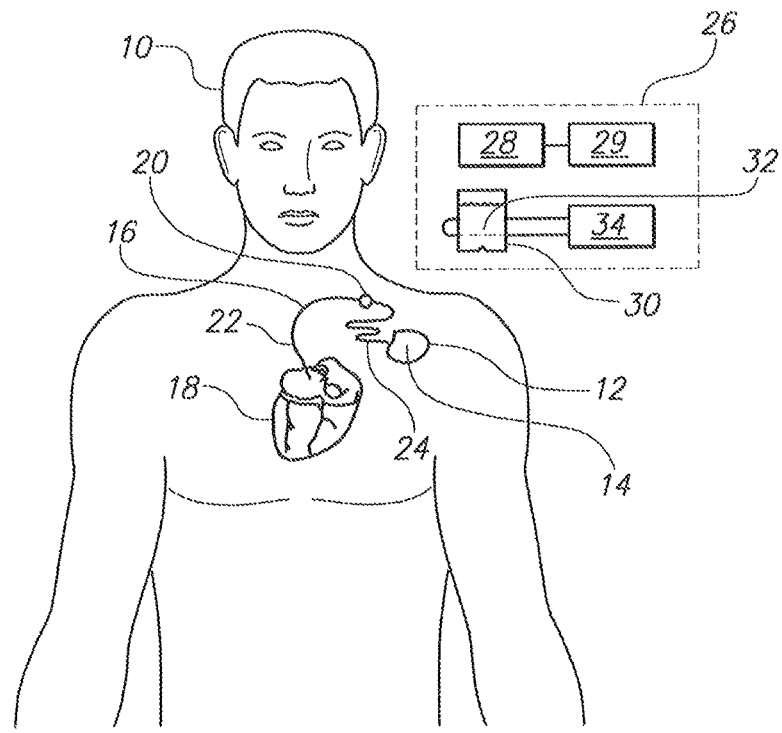
FIG. 1 depicts a medical device implanted in a patient that includes an electronic device and a lead together with a system for testing a proximal segment of the lead while a distal segment remains implanted in the patient's body.

Referring initially to FIG. 1, a patient 10 is shown with a medical device 12 implanted in his body. As shown, the medical device 12 includes an electronic device 14 and an elongated lead 16. For normal operation of the medical device 12, the proximal end of the lead 16 is electrically connected to the electronic device 14 and the distal end of the lead 16 is attached to the patient's heart 18. For example, the medical device 12 can be a conventional device such as an artificial cardiac pacemaker, an implantable cardioverter defibrillator (ICD), a combination pacemaker/defibrillator or any other implantable medical device known in the pertinent art which has an implanted lead that sends electrical impulses to or receives electrical signals from a patient's organ such as the heart 18.

For the above-described purposes, the electronic device 14 typically includes an internal battery, pulse generating circuit, a sensor for monitoring the electrical activity of the heart and a programmable microcontroller. With this arrangement, the electronic device 14 can be used to send electrical impulses to the heart 18 via lead 16 and/or monitor heart activity. Although only one lead 16 is shown, it will be appreciated that more than one lead may be used with the electronic device 14 to stimulate/control heart muscle activity of a patient 10.

Continuing with FIG. 1, it can be seen that the lead 16 is shown to extend continuously from the electronic device 14 to the heart 18 without splices or connections. Typically, when the medical device 12 is implanted, the distal end of lead 16 is inserted into the left subclavian vein, guided into a heart chamber (atrium or ventricle) and affixed to the heart. For example, the lead 16 may be either an active fixation lead or a passive fixation lead.

FIG. 1 also shows that a midsection of the lead 16 may be affixed to the patient using a tie-down 20, for example, sutures. Anatomically, as shown, the tie-down 20 is typically located near the area where the lead 16 enters the subclavian vein. With this arrangement, the lead 16 is functionally divided into a distal segment 22 and proximal segment 24. As shown, the distal segment 22 extends from the tie-down 20 to the heart 16 arid the proximal segment 24 extends from the tie-down 20 to the electronic device 14. The electronic device 14, in turn, is typically implanted in a subcutaneous pocket that is located above the muscles and bones of the chest (i.e. near the collar bone), and below the subcutaneous fat of the chest wall. As described above, the tie-down 20 stabilizes the distal segment 22 against movement while allowing the proximal segment 24 to be flexible. Moreover, as shown, the proximal segment 24 may typically include several centimeters of slack (i.e. excess portion) between the tie-down 20 and electronic device 14.

FIG. 1 also shows a system 26 for testing a proximal segment 24 of the lead 16 while a distal segment 22 remains implanted in the patient 10. As shown, and described in detail below, the system 26 includes a monitor 28, optional pulse generator 29 (for use with pacemaker dependent patients), a container 30 holding a conductive fluid 32 and a voltage source 34 for establishing a current in the conductive fluid 32.

Figure 2:
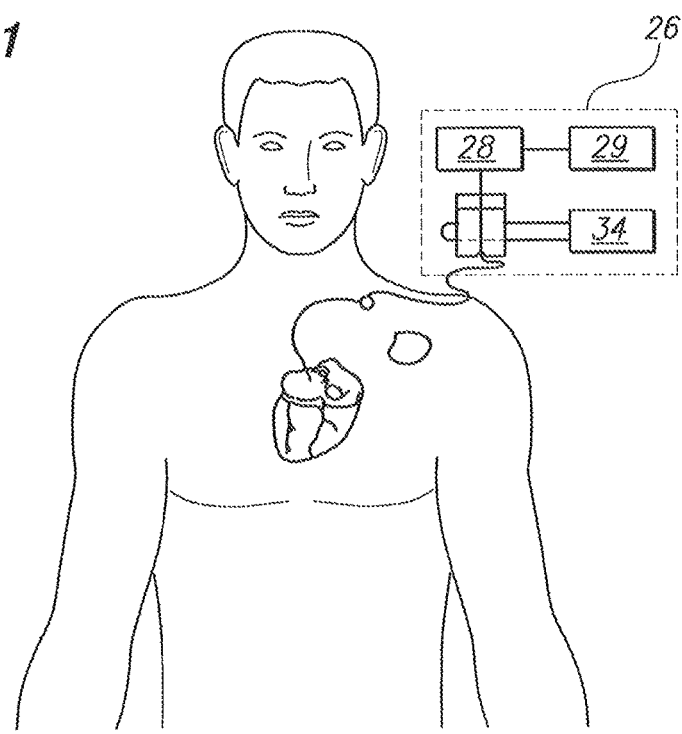
FIG. 2 depicts the patient and medical device of FIG. 1 during testing of the proximal lead segment by a system in accordance with the present invention.
Figure 3:
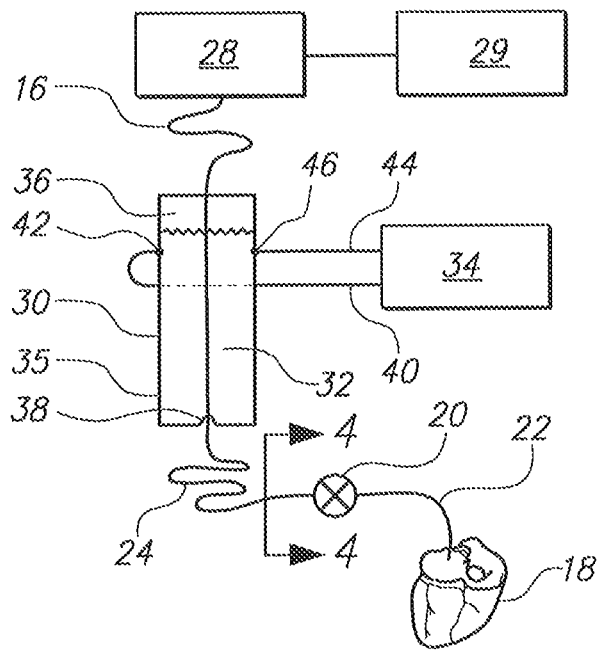
FIG. 3 is a schematic presentation of the components of the system shown during a test procedure which is performed in accordance with the present invention.

FIGS. 2 and 3 illustrate the system 26 during a test of a lead 16. In more detail, it can be seen that the container 30 has a wall 35 that surrounds a chamber 36. Also shown, the container 30 is provided to hold an electrically conductive fluid 32, such as a saline solution. An access port 38 is formed in the wall 35 to allow the proximal end of the lead 16 to be passed into the chamber 36 and through the fluid 32, as shown.

FIGS. 2 and 3 also illustrate that the system 26 includes a voltage source 34 that is connected via wire 40 to a cathode 42 and via wire 44 to anode 46. As shown, cathode 42 and anode 46 can be attached to wall 35 (or immersed in fluid 32) to generate an electrical current, which, as shown, can flow through the fluid 32 in a direction that is substantially orthogonal to the direction that lead 16 extends in chamber 36. Typically, the anode is spaced from the cathode by about 1 cm and the electric current is pulsed having a pulse duration of in the range of approximately 1 ms to 2 ms.

Figure 4:
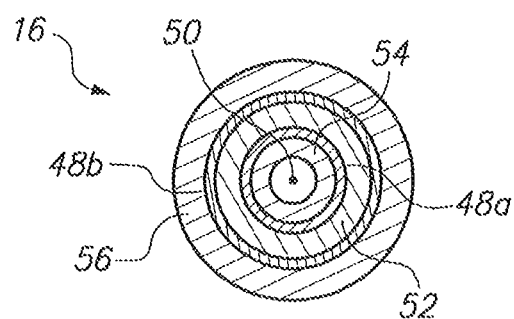
FIG. 4 is a cross sectional view of the coaxial electrical lead shown in FIG. 3 as seen along the line 4-4 in FIG. 3.

FIG. 4 illustrates that a typical bipolar lead 16 includes two electrode wires, an inner electrode wire 48*a* and an outer electrode wire 48*b*, that are cylindrically shaped and are coaxially aligned along the axis 50 of the electrical lead 16. As shown, an intermediate layer of insulation 52 separates electrode wire 48*a* from electrode wire 48*b*, and an inner layer of insulation 54 serves to encapsulate electrode wire 48*a* and an outer layer of insulation 56 serves to encapsulate electrode wire 48*b*.

Figure 5:
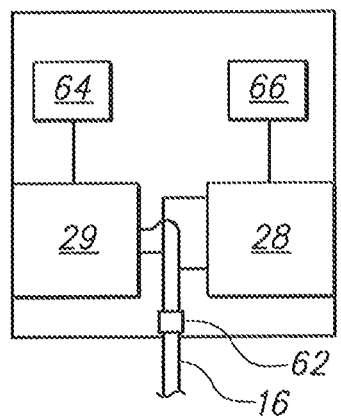
FIG. 5 is a schematic view of a monitor/pulse generator for use in the system shown in FIGS. 1-4.

Referring now to FIG. 5, a more detailed schematic of the monitor 28/pulse generator 29 is shown. As shown, the coaxial lead 16 can be plugged into a coaxial receptacle 62 in the monitor 28/pulse generator 29 which then serves to connect the pulse generator 29 and monitor 28 to the wires in the lead 16. A user input 64 which can consist of knobs, buttons, a touchscreen, etc, can be provided to adjust one or more pulse parameters of the pulses output by the pulse generator 29 such as pulse amperage in mA, pulse duration, and pulse rate or frequency. The monitor 28 can include a monitoring circuit such as a voltmeter or other instrument for determining the impedance in the lead 16, and can output a signal, alarm or reading to indicator 66.

The operation of the system 26 can best be appreciated with initial cross-reference to FIGS. 1 and 2. As shown there, the electronic device 14 and proximal segment 24 of the lead 16 are first surgically exposed. Next, the proximal end of the lead 16 is disconnected from the implanted electronic device 14. Once disconnected, the proximal end of the lead 16 is inserted into access port 38 (see FIG. 3), passed through the fluid 32 and plugged into the receptacle 62 (see FIG. 5).

With the proximal end of the lead 16 plugged into the monitor 28 (and optional pulse generator 29), the voltage source 34 can be activated to produce a voltage across electrodes (i.e. cathode 42 and anode 46). For example, a series of relatively low voltage electrical pulses can be applied to the electrodes to produce an electrical current passing through the fluid 32. With the voltage source 34 activated, the proximal segment 24 of the lead 16 can be slowly drawn through the fluid 32 and between the electrodes (i.e. cathode 42 and anode 46). As this is done, an interrupt signal will be received by the monitor 28 indicating that the electrical lead is defective whenever there is a break in the lead insulation.

Figure 6:
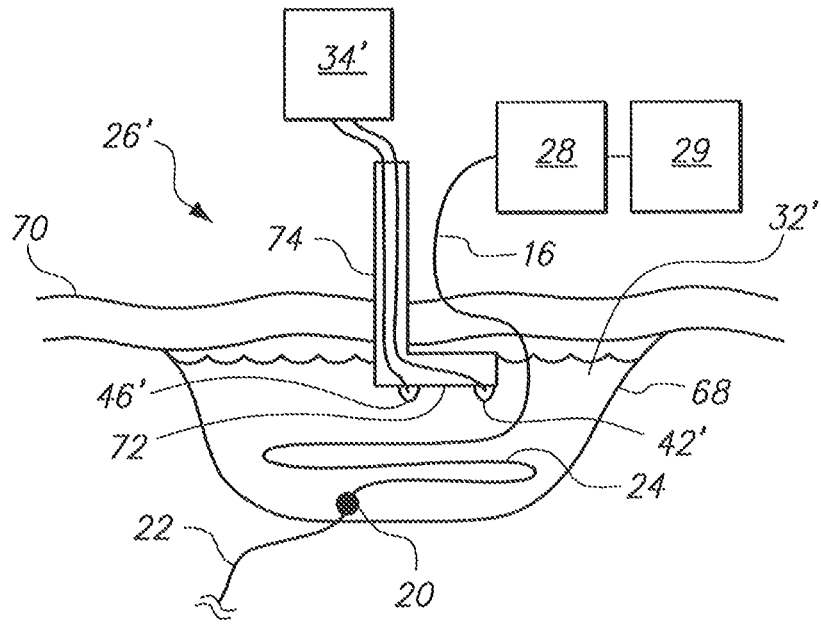
FIG. 6 illustrates another embodiment of the present invention in which lead insulation is tested, in situ, in a subcutaneous pocket of a patient.

In the case where the patient is pacemaker dependent, one or more test pulse(s)/pacing pulse(s) can be generated by the pulse generator 29 and sent through the lead 16. For example, the test pulse can be above or below a capture threshold necessary to stimulate a heart chamber to contract. For example, the test pulse can have a pulse duration in the range of approximately 0.4 ms to 0.5 ms. As the proximal segment 24 of the lead 16 is slowly drawn through the fluid 32 and between the electrodes (i.e. cathode 42 and anode 46), an interrupt signal will be received by the monitor 28 whenever the current in the conductive fluid 32 interferes with the test/pacing signal. Specifically, the monitor 28 will receive an interrupt signal indicating that the electrical lead 16 is defective whenever there is a break in the lead insulation, FIG. 6 illustrates another embodiment of the present invention in which the insulation of a proximal segment 24 of a lead 16 is tested, in situ, in a subcutaneous pocket 68 of a patient. As described earlier with reference to FIG. 1, a midsection of the lead 16 may be affixed to the patient using a tie-down 20, for example, sutures. Anatomically, as shown, the tie-down 20 is typically located near the area where the lead 16 enters the subclavian vein, With this arrangement, the lead 16 is functionally divided into a distal segment 22 and proximal segment 24. As shown in FIG. 1, the distal segment 22 extends from the tie-down 20 to the heart 18 and the proximal segment 24 extends from the tie-down 20 to the electronic device 14. The electronic device 14, in turn, is typically implanted in a subcutaneous pocket that is located above the muscles and bones of the chest (i.e. near the collar bone), and below the subcutaneous fat of the chest wall. As further described above, the tie-down 20 stabilizes the distal segment 22 against movement while allowing the proximal segment 24 to be flexible. Moreover, as shown in FIG. 1 and FIG. 6, the proximal segment 24 may typically include several centimeters of slack (i.e. excess portion) between the tie-down 20 and electronic device 14.

FIG. 6 also shows a system 26' for testing a proximal segment 24 of the lead 16 while a distal segment 22 remains implanted in the patient 10. As shown, and described in detail below, the system 26 includes a monitor 28 and optional pulse generator 29 (for use with pacemaker dependent patients), both as described above. For this embodiment shown in FIG. 6, an electrically conductive fluid 32' such as saline is disposed (i.e. poured or injected) within a pocket 68 that is established beneath the skin 70 of the patient. For example, the subcutaneous pocket used to implant the electronic device 14 (see FIG. 1) may be used.

Also shown in FIG. 6, for this embodiment, an anode 46' and cathode 42' that are electrically connected to a voltage source 34' are spaced-apart and attached to a non-conductive tip 72 of a retractor 74. For example, the retractor 74 may be made of medical grade plastic. As shown, the tip 72 of the retractor can be L-shaped and the anode 46' and cathode 42' are attached to the bottom face of the L-shaped tip 72. Typically, the anode 46' and cathode 42' are separated by about 1 cm. With this arrangement, the retractor 74 can be used to align the anode 46' and cathode 42' in a direction substantially parallel to a plane containing a portion of the lead 16 undergoing testing, as shown, to improve electrical coupling, between the lead 16 and anode 46' and cathode 42'.

With the proximal end of the electrical lead 16 electrically connected to the monitor 28, the retractor tip 72 is immersed in the electrically conductive fluid 32' to generate a current, e.g. pulsed current, in the fluid 32'. As the current is generated in the fluid 32', an interrupt signal will be received by the monitor 28 indicating that the electrical lead is defective if there is a break in the lead insulation. For a pacemaker dependent patient, a pulse generator 29, as described above, can be connected to the proximal end of the electrical lead 16. For this case, an interrupt signal will be received by the monitor 28 whenever the current in the fluid 32' interferes with the test/pacing signal in the lead 16 from the pulse generator 29. Specifically, the monitor 28 will receive an interrupt signal indicating that the electrical lead 16 is defective whenever there is a break in the lead insulation.

While the particular Extracorporeal Unit for Inspecting the Insulation of an Electrical Wire of an Implanted Medical Device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for testing the electrical integrity of an elongated electrical lead when the lead is used with an implanted electronic device to stimulate/control heart muscle activity of a patient, wherein the electrical lead defines an axis and has insulated electrode wires extending between a proximal end and a distal end of the lead to establish an electrical connection between the electronic device and the heart muscle of the patient, and wherein the electrical lead includes a distal segment of the electrical lead extending between a tie-down point to the heart muscle, and a proximal segment of the electrical lead extending between the tie-down point and the electronic device, the system comprising:
   a monitor selectively connected to at least one of the electrode wires at the proximal end of the lead configured to monitor electrical activity in the lead while the proximal end of the lead is disconnected from the electronic device and while the distal end of the lead remains tied down to the heart muscle;
   a pulse generator connected to the monitor configured to provide a pulse output to the lead having predetermined pulse parameters during the disconnect of the lead from the electronic device;
   a container having a wall surrounding a chamber configured to hold an electrically conductive solution therein, and wherein an access port is formed in the wall of the container configured to pass the lead into the chamber of the container, wherein the electrically conductive solution is positioned to surround at least a portion of the proximal segment of the lead as the proximal segment is drawn portion by portion, through the conductive solution; and
   a voltage source having a cathode and an anode, wherein the cathode and the anode of the voltage source are respectively connected to the wall of the container to establish an electrical current through the solution and cause an interrupt signal that is received by the monitor when there is a break in the insulation of the proximal segment of the lead.

2. A system as recited in claim 1 wherein the electrically conductive solution is a saline solution.

3. A system as recited in claim 1 wherein the electrode wires are cylindrically shaped and are coaxially aligned along the axis of the electrical lead.

4. A system as recited in claim 3 wherein the electrode wires of the electrical lead include an outer electrode wire and an inner electrode wire, and the monitor is electronically connected to the respective electrode wires of the electrical lead at the proximal end of the electrical lead.

5. A system as recited in claim 1 wherein the proximal segment of the electrical lead includes an excess portion of the lead to provide for a required flexibility of the proximal segment, and wherein the excess portion is implanted in a subcutaneous pocket between the tie-down point and the electronic device.

6. A system as recited in claim 1 wherein the electronic device is selected from a group of electronic devices consisting of a pacemaker pulse generator and a defibrillator pulse generator.

7. A system as recited in claim 1 further comprising a device connected to the proximal end of the lead for sending a test pulse through the lead and wherein the anode and cathode are positioned to establish an electrical current through the solution and cause an interrupt signal to be received by the monitor to indicate a defective lead when a break in the insulation of the lead causes the current in the solution to interfere with the test pulse from the device.

8. A system for testing the integrity of insulation in an electrical lead and wherein the electrical lead includes a distal segment of the electrical lead extending between a tie-down point to the heart muscle, and a proximal segment of the electrical lead extending between the tie-down point and an electronic device, while the proximal segment of the electrical lead is disconnected from the electronic device, and the distal segment of the lead remains attached to a patient's heart, the system comprising;
   a voltage source having a cathode and an anode;
   an electrically conductive solution surrounding at least a portion of the proximal segment of the lead, the solution electrically connected to the cathode and anode to establish an electrical current through the solution;
   a monitor connected to an electrode wire of the lead;
   a container having a wall surrounding a chamber configured to hold the electrically conducive solution, wherein the cathode and the anode of the voltage source are respectively connected to the wall of the container and wherein an access port is formed in the wall of the container configured to pass the proximal segment into the chamber of the container and configured to draw the proximal segment of the electrical lead, portion by portion, through the conductive solution; and
   a pulse generator connected to the monitor configured to provide a pulse output to the lead during the disconnect of the lead from the electronic device, wherein the pulse output has predetermined pulse parameters and the monitor is configured to output an alarm signal in response to an input from the lead indicating that the current in the solution is generating an interrupt signal in the lead due to an insulation breach.

9. A system as recited in claim 8 further comprising a pulse generator connected to a proximal end of the lead for sending a test pulse through the lead with the monitoring circuit connected to the lead and configured to output an alarm signal in response to an input from the lead indicating that the current in the solution is generating an interrupt signal in the lead interfering with the test pulse from the pulse generator due to an insulation breach.

10. A system as recited in claim 9 wherein the test pulse is above a capture threshold necessary to stimulate heart chamber contraction.

11. A system as recited in claim 9 wherein the test pulse has a pulse duration in the range of approximately 0.4 ms to 0.5 ms.

12. A system as recited in claim 8 wherein the voltage source produces a pulsed current in the electrically conductive solution.

13. A system as recited in claim 12 wherein the pulsed current has a pulse duration In the range of approximately 1 ms to 2 ms.

14. A system as recited in claim 8 wherein the lead is a bipolar pacemaker lead.

15. A method for testing the integrity of insulation in a proximal segment of an electrical lead when the electrical lead is disconnected from an electronic device while a distal segment of the lead remains attached to a patient's heart, the method comprising the steps of:
   surrounding at least a portion of the proximal segment of the lead with an electrically conductive solution;
   sending a pulse output to the lead having predetermined pulse parameters during the disconnect of the lead from the electronic device;

a container having a wall surrounding a chamber configured to hold the electrically conductive solution, wherein a cathode and an anode of a voltage source are respectively connected to the wall of the container and wherein an access port is formed in the wall of the container;

passing the lead through the access port of the container into the chamber of the container;

establishing an electrical current through the solution;

drawing the proximal segment of the electrical lead, portion by portion, through the conductive solution;

monitoring an output from an electrode wire of the lead; and generating an alarm signal in response to an input from the lead indicating that the current in the solution is generating an interrupt signal in the lead due to an insulation breach.

16. A method as recited in claim 15 further comprising the step of connecting a pulse generator to a proximal end of the lead and sending a test pulse through the lead and wherein the alarm signal is generated in response to an output from the lead indicating that the current in the solution is interfering with the test pulse from the pulse generator due to an insulation defect.

17. A method as recited in claim 15 wherein the passing step is performed while a distal end of the lead is attached to a patient's heart.

18. A method as recited in claim 15 wherein only a portion of the proximal segment of the lead is surrounded by the solution at a time.

* * * * *

UNITED STATES PATENT AND TRADEMARK OFFICE
CERTIFICATE OF CORRECTION

PATENT NO. : 10,232,184 B2
APPLICATION NO. : 13/607309
DATED : March 19, 2019
INVENTOR(S) : Guy P. Curtis Page 1 of 1

It is certified that error appears in the above-identified patent and that said Letters Patent is hereby corrected as shown below:

In the Specification

Column 2, Line 37 - after the word "solution." and before the word "Also" DELETE "P".

Column 4, Line 35 - after the word "heart" and before the word "the" DELETE "16 arid" and INSERT --18 and--.

Column 5, Line 20 - after the word "etc" and before the word "can" DELETE "," and INSERT --.--.

Signed and Sealed this
Eighteenth Day of June, 2019

Andrei Iancu
*Director of the United States Patent and Trademark Office*